(12) United States Patent
Kuniya et al.

(10) Patent No.: US 8,040,109 B2
(45) Date of Patent: Oct. 18, 2011

(54) BATTERY TERMINAL INSPECTION APPARATUS, INSPECTION METHOD, AND CYLINDRICAL DRY BATTERY

(75) Inventors: Shigeyuki Kuniya, Shizuoka (JP); Yuji Tsuchida, Shizuoka (JP); Tatsuya Yamazaki, Shizuoka (JP)

(73) Assignee: FDK Energy Co., Ltd., Shizuoka (JP)

( * ) Notice: Subject to any disclaimer, the term of this patent is extended or adjusted under 35 U.S.C. 154(b) by 189 days.

(21) Appl. No.: 12/223,220

(22) PCT Filed: Jun. 23, 2006

(86) PCT No.: PCT/JP2006/312584
§ 371 (c)(1), (2), (4) Date: Dec. 16, 2008

(87) PCT Pub. No.: WO2007/086154
PCT Pub. Date: Aug. 2, 2007

(65) Prior Publication Data
US 2010/0103423 A1    Apr. 29, 2010

(30) Foreign Application Priority Data

Jan. 25, 2006   (JP) ................. 2006-016780

(51) Int. Cl.
H02J 7/00 (2006.01)
H02J 7/14 (2006.01)
(52) U.S. Cl. ............................. 320/137; 320/107
(58) Field of Classification Search .......... 356/402, 356/445; 320/112, 137, 132; 250/370.13, 250/370.14; 324/426, 132, 427, 430; 429/180, 181, 100
See application file for complete search history.

(56) References Cited

U.S. PATENT DOCUMENTS
3,875,404 A * 4/1975 Fletcher et al. ............ 250/214.1
(Continued)

FOREIGN PATENT DOCUMENTS
JP     4-79277 U     7/1992
(Continued)

*Primary Examiner* — Sang Nguyen
(74) *Attorney, Agent, or Firm* — Harness, Dickey & Pierce, PLC

(57) ABSTRACT

Poor contact on a terminal face that is likely to especially occur with a dry battery with low electromotive force can be appropriately inspected and suppressed. Moreover, the inspection can be highly efficiently performed in a non-contacting state. Also, a cylindrical dry battery in which the poor contact on the terminal face is certainly suppressed is provided. An apparatus 50 that inspects an electric contact at an outer surface of a positive terminal 12 and a negative terminal 32 of a dry battery 10, includes: a light-emitting section 51 that makes a light incident on a part to be measured on a terminal face of the battery; a light-receiving section 52 that detects a reflection state of the light from the part to be measured, and a measurement processing section 55 that quantifies gloss level of the part to be measured based on detection with the light-receiving section 52, wherein evaluation data of the electric contact is obtained with measurement values of the gloss level.

5 Claims, 2 Drawing Sheets

U.S. PATENT DOCUMENTS

| | | | |
|---|---|---|---|
| 4,981,764 A * | 1/1991 | Dattilo | 429/50 |
| 5,014,549 A * | 5/1991 | Morley et al. | 73/118.02 |
| 5,196,898 A * | 3/1993 | Tamura et al. | 356/70 |
| 5,367,379 A | 11/1994 | Makino | |
| 5,510,644 A * | 4/1996 | Harris et al. | 257/458 |
| 5,739,916 A * | 4/1998 | Englehaupt | 356/414 |
| 5,949,219 A * | 9/1999 | Weiss | 320/136 |
| 6,127,797 A * | 10/2000 | Walker | 320/101 |
| 6,433,667 B1 * | 8/2002 | Isomichi | 340/7.2 |
| 6,520,018 B1 | 2/2003 | Flores-Lira | |
| 6,536,318 B1 * | 3/2003 | Bender | 83/34 |
| 6,911,803 B2 * | 6/2005 | Hanson | 320/132 |
| 6,919,725 B2 * | 7/2005 | Bertness et al. | 324/433 |
| 7,034,541 B2 * | 4/2006 | Bertness et al. | 324/426 |
| 7,129,706 B2 * | 10/2006 | Kalley | 324/426 |
| 7,202,689 B2 * | 4/2007 | Condon et al. | 324/750.3 |
| 7,388,383 B2 * | 6/2008 | Kawakami et al. | 324/430 |

FOREIGN PATENT DOCUMENTS

| | | |
|---|---|---|
| JP | 2000-048799 | 2/2000 |
| JP | 2000-138056 | 5/2000 |
| JP | 2001-118609 A | 4/2001 |
| JP | 2002-124218 | 4/2002 |
| JP | 2002117911 A * | 4/2002 |

* cited by examiner

BATTERY TERMINAL INSPECTION APPARATUS, INSPECTION METHOD, AND CYLINDRICAL DRY BATTERY

TECHNICAL FIELD

The present invention relates to battery terminal inspection apparatuses and inspection methods for inspecting an electric contact at an outer surface of a positive terminal and a negative terminal of a dry battery, and cylindrical dry batteries, and more particularly to inventions that are effective when applied to a dry battery used in heavy-load electric discharge applications, for example, the cylindrical dry battery such as an alkaline dry battery.

BACKGROUND ART

Cross-Reference to Related Applications

This application claims priority upon Japanese Patent Application No. 2006-16780 filed on Jan. 25, 2006, which is herein incorporated by reference.

A cylindrical alkaline dry battery such as LR6 has a configuration in which a bottomed cylindrical cathode can, also serving as a cathode current collector, is loaded with a cathode mixture, a separator, and a gelled anode mixture, together with an alkaline electrolyte, and thereby power generating elements are formed, and an opening of the cathode can is sealed using a negative terminal plate and a gasket.

This type of alkaline dry battery is formed with a positive terminal and a negative terminal on both ends of a cylinder, and is used in a state of being contained in a battery holder (or a battery case) of a device with both of the positive terminal and the negative terminal contacting the device-side terminals. Generally, the device-side terminals are spring biased so as to press in contact with the battery-side terminals. In the case where terminal faces of the battery-side are formed with good conductive faces, the continuity between the battery and the device also becomes good.

However, generally, since an electromotive force of the dry battery is a low-voltage such as 1.5 V, the continuity between the battery and the device is apt to become unstable because contact resistance increases. Thus, to ensure the continuity, for example, performing roughening, or a plating process or the like on the terminal face of the battery has been conventionally suggested (for example, JP-A-2002-124218, JP-A-2000-138056, and JP-A-2000-48799).

DISCLOSURE OF INVENTION

Problems to be Solved by the Invention

It has been made clear by the inventors or the like that there are the following problems in the conventional art described above.

That is, the inventors or the like have found, from years of research and experience, that the terminal face of the dry battery cannot always assure fine electric contact, for example, even if the terminal face of the dry battery is roughened or applied with the plating process or the like. This is supported by the fact that, even currently, improvements and developments are still being made regarding processing and treating of the terminal face of the dry battery.

As described above, generally, the electromotive force of the dry battery is a low-voltage such as 1.5 V. However, in such a low-voltage area, faulty energization, which cannot be solved just with a conductive material forming the surface of the terminal, is likely to occur. That is, since there are many unstable factors in the electric contact at the low-voltage area of several volts, fine electric contact cannot be assured only with the surface material of the terminal.

Therefore, with conventional dry batteries in which the electric contact of the terminal face has been attempted to be improved by a roughening process or a plating process or the like on the terminal face of the dry battery, the occurrence of the contact failure of the terminal at the stage where the battery is loaded into the device and actually used could not be certainly avoid.

This contact failure of the battery terminal is unstable and low in reproducibility, and, for example, it is quite often the case that trouble of contact failure occurs for the first time at the time of actual use, even when the contact is normal in the inspection measuring the electromotive force. Regarding causes of the occurrence of such uncertain contact failure, in addition to the low-voltage of the electromotive force of the dry battery, increase of contact resistance due to an oxide film generated on the terminal surface of the dry battery or dirt of adherents such as oil can be considered.

It had become clear that the oxide film and dirt on the terminal face is torn more or less by the roughening process of the terminal face, however this is not perfect, and stops short of certainly reducing the contact resistance. However, with the conventional dry batteries, there was a problem that an appropriate inspection regarding the electric contact failure due to the oxide film or oil and the like was not performed, and therefore the contact failure was likely to occur at the time of actual use.

On the other hand, in recent years, a portable electronic device with a large consumption current, for example a digital camera or the like, have become popular. In accordance with this, heavy-load electric discharge performance of a dry battery used in that device has become to be considered as important.

In order to meet this situation, an alkaline dry battery in which high-current electric discharge is possible by using nickel oxyhydroxide as a cathode active material or the like has started to become provided. In these high-performance dry batteries, the quality of the electric contact at the terminal face of the battery becomes a particularly large problem. However, since an appropriate inspection cannot be performed regarding the electric contact failure due to the oxide film or oil and the like, trouble of decrease in the electric discharge performance and the like in use of a heavy-load electric discharge device could not be certainly prevented.

Also, the alkaline dry batteries currently on the market are mass-produced products, which are shipped to a secondary market in units of a large number. In such a case, as the performance of the battery, the performance as a single battery is important, but also the statistical performance in a state of being in a large number, that is, as a battery group, is important. The fraction defective is particularly seen as a problem in the performance of the battery group, and in the conventional battery group, there was a problem that the fraction defective of the electric contact due to the oxide film or oil and the like was high.

The present invention has been developed in consideration of the above problems, and an object thereof is to provide a battery terminal inspection apparatus and an inspection method that can appropriately and highly efficiently inspect and suppress the contact failure on the terminal face that is likely to occur especially at the dry battery with low electromotive force. Further, the object is to provide a cylindrical dry battery in which the contact failure on the terminal face is certainly suppressed.

Objects and configurations of the present invention other than that stated above will become clear from the description of the present specification and the accompanying drawings.

Means for Solving the Problems

The present invention provides the following means for solving the problems.

(1) A battery terminal inspection apparatus that inspects an electric contact at an outer surface of a positive terminal and a negative terminal of a dry battery, including:

a light-emitting section that makes a light incident on a part to be measured on a terminal face of the battery;

a light-receiving section that detects a reflection state of the light from the part to be measured; and a measurement processing section that digitizes the reflection state of the light from the part to be measured based on detection with the light-receiving section, wherein evaluation data of the electric contact is obtained with measurement values of the reflection state of the light.

(2) A battery terminal inspection apparatus, wherein with the above apparatus (1), gloss level, as the reflection state of the light from the part to be measured, is measured with a received light quantity of a reflected light and the evaluation data of the electric contact is obtained with the measured received light quantity.

(3) A battery terminal inspection method, wherein regarding a positive terminal and a negative terminal of a dry battery, an increase of contact resistance due to an oxide film generated on the outer surface or dirt of adherents such as oil is inspected using an apparatus according to the above apparatus (1) or (2).

(4) A battery terminal inspection method, wherein a received light quantity of the reflected light is measured in the following measurement conditions, by using a digital color differentiation sensor as an apparatus according to the above apparatus (1) or (2).

[Measurement Conditions]
Colors of light source: red LED, green LED, blue LED
Sensor type: red LED, green LED, blue LED light source reflecting type photoelectric sensor attached with amplifier
Distance from a sensor head to a sample: 20 mm
Angle: at right angles to the sensor head
Measuring spot diameter: 3.5 mm
Measurement time: 0.5-1 minute
Standard color face setting: the received light quantity is 300 on a specular surface
Measurement condition: still (5) A cylindrical dry battery, wherein an average received light quantity at an outer surface of a positive terminal and a negative terminal is within a range of 20-60 by the received light quantity (300 in a specular surface) that is to be measured with the inspection method according to the above method (4).

EFFECT OF THE INVENTION

According to the present invention, it is possible to appropriately inspect and suppress contact failure on a terminal face, which is likely to particularly occur in a dry battery with low electromotive force. Moreover, the inspection can be performed highly efficiently in a non-contacting state. Further, it is possible to provide a cylindrical dry battery in which the contact failure on the terminal face is certainly suppressed.

Operations and/or effects other than above will become clear from the description of the present specification and the accompanying drawings.

Figure 1:
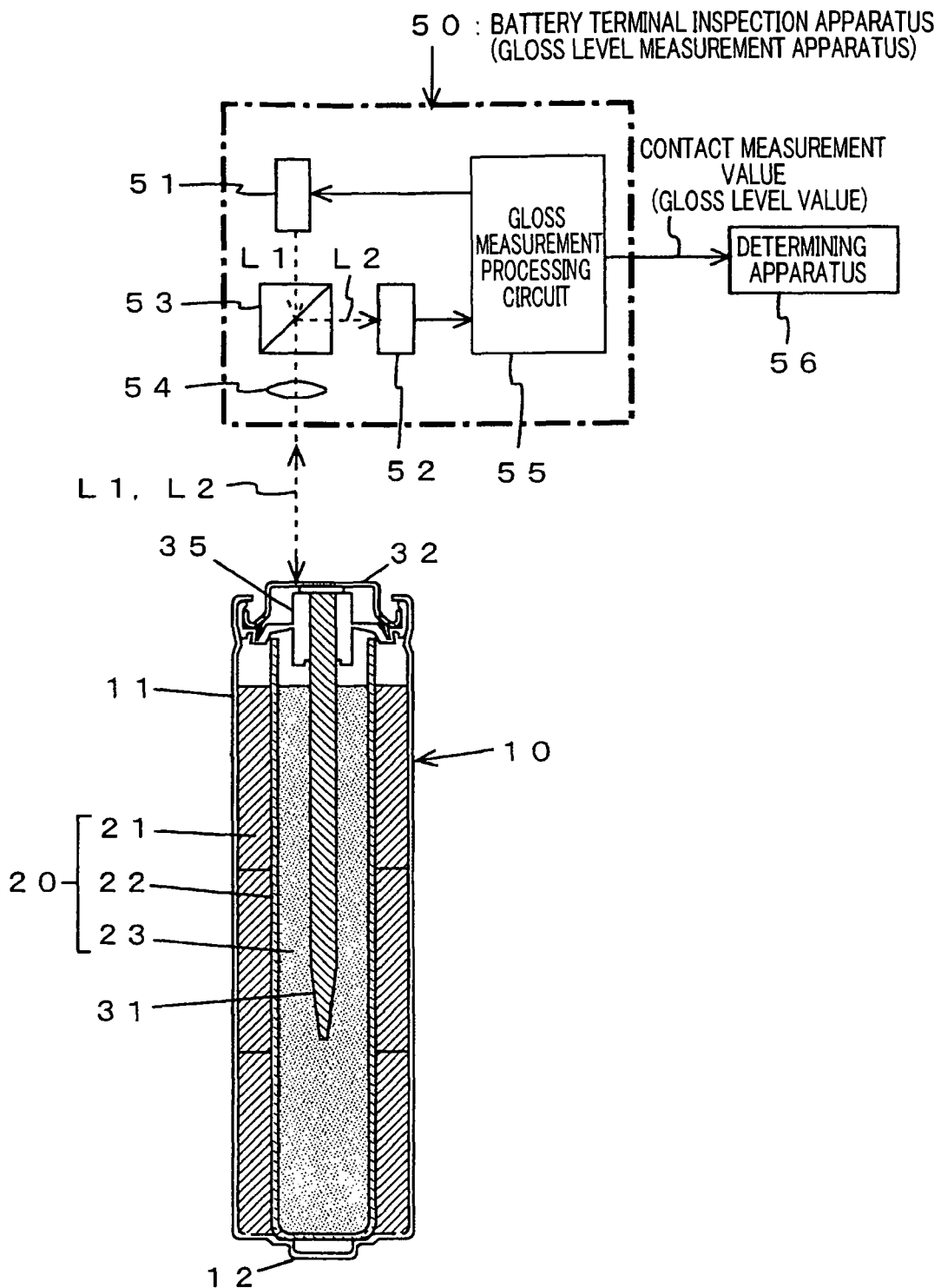
FIG. 1 is a conceptual diagram showing an embodiment of a battery terminal inspection apparatus, an inspection method, and a cylindrical dry battery according to the present invention.

EXPLANATION OF REFERENCE CHARACTERS 11 cathode can, 12 positive terminal part,
20 power generating elements, 21 cathode mixture,
22 separator, 23 anode mixture,
31 anode current collector, 32 negative terminal plate,
35 gasket, 50 battery terminal inspection apparatus,
51 light-emitting section, 52 light-receiving section,
53 beam splitter, 54 image-forming optical system,
55 gloss measurement processing circuit, 56 determining apparatus,
60 pedestal, 500 digital color differentiation sensor manufactured by KEYENCE CORPORATION,
501 sensor body, 502 light-emitting/receiving section,
503 connecting cable, L1 incident light, L2 reflected light.

BEST MODE FOR CARRYING OUT THE INVENTION

FIG. 1 shows an embodiment of a battery terminal inspection apparatus 50, an inspection method, and a cylindrical dry battery 50 to which technology of the present invention has been applied.

First, the cylindrical dry battery 10 illustrated in FIG. 1 is a LR6 type alkaline dry battery, and in a bottomed cylindrical metallic cathode can 11, power generating elements 20 constituted by a cathode mixture 21, a separator 22, and an anode mixture 23 are contained together with an alkaline electrolyte.

The cathode can 11 serves both as a cathode current collector and a positive terminal, and a protruded positive terminal part 12 is integrally formed by pressing on a bottom section thereof. An opening section of the cathode can 11 is sealed with a negative terminal plate 32 and a resin gasket 35. An anode current collector 31 in a bar shape is placed in an inner side of the negative terminal plate 32. And this current collector 31 is inserted into the gelled anode mixture 23.

The cathode mixture 21 is an annular solid which is made by cylindrically molding a mixture in which conductivity assistant lead such as graphite is added to cathode active material. Manganese dioxide (EMD) and/or EMD and nickel oxyhydroxide (NiOOH) are used for such cathode active material.

A battery terminal inspection apparatus 50 is constituted by a light-emitting section 51, a light-receiving section 52, a beam splitter 53, an image-forming optical system 54, a gloss measurement processing circuit 55, and a determining apparatus 56 or the like.

The light-emitting section 51 uses a semiconductor laser or a light-emitting diode as a light source, and makes a spotlight L1 incident on a part to be measured on a terminal surface of the battery 10 (outer surface of the negative terminal plate 32 in shown example), via the beam splitter 53 and the image-forming optical system 54.

The light-receiving section 52 uses one or a plurality of optical sensors, or an image pickup device such as a CCD, and via the image-forming optical system 54 and the beam splitter 53, receives and detects the state of reflection of the spotlight L1 that was made incident on the part to be measured. L2 shows the reflected light.

There are a specular reflected light and a diffused light in the reflected light L2. The optical system 54 and the light-receiving section 52 are configured so that only the specular reflected light is selectively received and detected. By selectively measuring only an amount of a light received of the specular reflected light, the gloss level of the part to be measured can be measured from the measured amount of the light received.

The gloss measurement processing circuit 55 performs processing that digitizes the reflection state of the part to be measured into the gloss level, based on receiving and detecting light at the light-receiving section 52. By this gloss measurement processing circuit 55, the reflection state of the part to be measured is digitized and outputted as the gloss level. The determining apparatus 56 determines whether or not the digitized data is within a predetermined range.

The battery terminal inspection apparatus 50 is configured using a gloss level measuring apparatus. The light reflection state on a battery terminal face is measured as the gloss level, and the inventors have found that the gloss level reflects remarkably well the quality of the electric contact. That is, degradation of the electric contact due to the oxide film generated on the outer surface of the battery terminal or dirt by adherents such as oil can be appropriately determined with the measurement value of the gloss level.

As described above, the electric contact at the outer surface of the positive terminal part 12 and the negative terminal plate 32 of the dry battery 10 can be inspected by measuring the light reflection state, especially the gloss level, on the outer surface. Therefore, poor contacting rate of the terminal can be greatly reduced with the dry battery that has been adjusted and/or selected so that the average gloss level, that is, the received light quantity of the reflected light, on the outer surface of the positive terminal and the negative terminal is within a specific range.

It is possible to apply a commercially available ready-made product to the gloss level measuring apparatus that configures the battery terminal inspection apparatus 50. As the ready-made gloss level measuring apparatus, a digital color differentiation sensor manufactured by KEYENCE CORPORATION (an amplifier: CZ-1, a sensor head: CZ-10) can be preferably used.

It has been confirmed that the battery terminal face of which the received light quantity of the reflected light measured by the digital color differentiation sensor manufactured by KEYENCE CORPORATION is to be within the range of 20-60 (300 in a specular surface) certainly has an excellent electric contact. This is conceivable because the state of the oxide film and dirt of adherents such as oil, which are causes of degrading the electric contact, are reflected with high reproducibly on the light reflection state, especially the gloss level, of the terminal face.

Therefore, in the case the digital color differentiation sensor manufactured by KEYENCE CORPORATION is used as the battery terminal inspection apparatus 50, by adjusting and/or selecting so that the average received light quantity at the outer surface of the positive terminal and the negative terminal is within the range of 20-60, poor contacting rate of the dry battery can be certainly suppressed.

Figure 2:
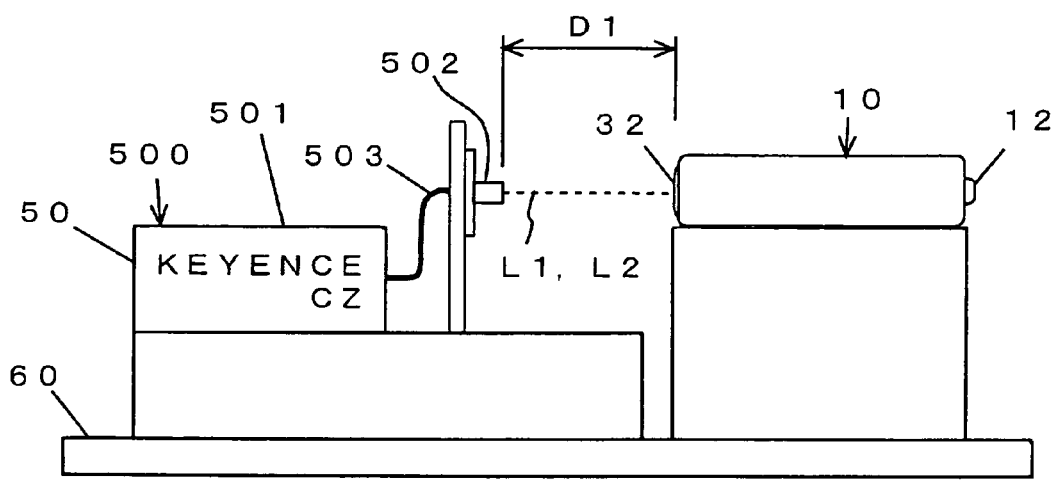
FIG. 2 is a side view showing a specific embodiment of a battery terminal inspection apparatus and an inspection method according to the present invention.

FIG. 2 shows a summary of the inspection apparatus 50 using the digital color differentiation sensor 500 manufactured by KEYENCE CORPORATION. The digital color differentiation sensor 500 is constituted by an amplifier (CZ-V1) 501, a sensor head (CZ-10) 502, and a connecting optical fiber 503, which are placed on an appropriate pedestal 60.

The light-emitting section that makes the spotlight L1 incident on the terminal face (32) of the dry battery 10, and the light-receiving section that receives the reflected light L2 are aggregated in the sensor head (CZ-10) 502. In the state of keeping a distance D1 between the sensor head (CZ-10) 502 and the terminal face to be measured (32) constant (20 mm), by measuring the received light quantity of the reflected light from the face of the terminal to be measured (32), the quality of the electric contact at the face of the terminal to be measured (32) can be appropriately determined by whether or not the received light quantity is within the predetermined range (20-60).

Here, it should be noted that, with the inspection method using the inspection apparatus 50, the quality of the electric contact can be inspected in a non-connecting state. Thus, a large amount of dry batteries in a mass production site can be inspected highly efficiently.

Examples

With the LR6 type alkaline dry batteries configured as having equal capacitance, a plurality of types of the dry batteries (samples 1-11) are formed so that only the quantity of reflected light received (the received light quantity of the reflected light) on the outer surface of the negative terminal and the positive terminal differ, and tests evaluating electric contact of terminals are performed on each battery.

In measuring the quantity of reflected light received, the digital color differentiation sensor manufactured by KEYENCE CORPORATION (the amplifier: CZ-1, the sensor head: CZ-10) is used in I (bright/dark) mode, and two parts of the positive terminal and the negative terminal respectively are measured. The measurement of the received light quantity is performed in the following conditions.

[Measurement Conditions]
Colors of light source: red LED, green LED, blue LED
Sensor type: red LED, green LED, blue LED light source reflecting type photoelectric sensor attached with amplifier
Distance from a sensor head to a sample: 20 mm
Angle: at right angles to the sensor head
Measuring spot diameter: 3.5 mm
Measurement time: 0.5-1 minute
Standard color face setting: the received light quantity is 300 on specular surface (complete specular surface)
Measurement condition: still In the evaluation test, the battery was mounted in a digital camera and the number of photos that can be taken was counted. The digital camera "DSC-H1" manufactured by SONY was used. Test conditions and shooting method are pursuant to CIPA standards of "Standard Procedure for Measuring Digital Still Camera Battery Consumption" (CIPA DC-002-2003), and the number of photos taken was counted under a temperature of 21 degrees C. The brightness at the time of shooting is about 750 lux and the shooting method is performed in the following procedures (1)-(3).
(1) Start
(2) Repeat 5 times of zoom, shooting with flash, zoom, shooting without flash. The time required is 5 minutes.
(3) Wait a 10-minutes pause period.

The number of photos taken by repeating (2), (3) is counted.

The above test results are shown in Table 1.

TABLE 1

The received light quantity at the terminal faces and the number of photos that can be taken

| Battery sample no. | Reflected light quantity (gloss level) | | | | | The number of photos taken |
|---|---|---|---|---|---|---|
| | Negative terminal | Average | Positive terminal | Average | | |
| 1 | 5 | 8 | 7 | 7 | 11 | 9 | 21 |
| 2 | 15 | 16 | 16 | 17 | 14 | 16 | 19 |
| 3 | 28 | 30 | 29 | 27 | 34 | 31 | 69 |
| 4 | 30 | 31 | 31 | 23 | 29 | 26 | 67 |
| 5 | 58 | 57 | 58 | 56 | 59 | 58 | 67 |
| 6 | 153 | 156 | 155 | 169 | 172 | 171 | 47 |
| 7 | 229 | 201 | 216 | 115 | 100 | 108 | 49 |
| 8 | 179 | 186 | 183 | 129 | 187 | 158 | 45 |
| 9 | 216 | 228 | 222 | 108 | 197 | 153 | 47 |
| 10 | 285 | 293 | 289 | 229 | 230 | 230 | 45 |
| 11 | 249 | 232 | 241 | 426 | 344 | 385 | 39 |

As shown in table 1, it is recognized that in a group of dry batteries of the present invention in which the quantity of reflected light received from the terminal face (300 in the specular surface) is within a range of 20-60 (samples 3-5), compared to the groups of dry batteries in which the quantity of reflected light received is out of such a range (samples 1, 2, and 6-11), the number of photos that can be taken has increased by about 40%.

As stated above, although the present invention has been explained based on its representative examples, various modes other than those stated above can be also achieved in this invention. For example, the battery terminal inspection apparatus 50 of this invention does not have to be a dedicated apparatus that has been manufactured as the gloss level measuring apparatus from the beginning, as long as it is an apparatus that can digitize and measure the light reflection state of the part to be measured.

INDUSTRIAL APPLICABILITY

The poor contact on the terminal faces that is likely to occur especially with a dry battery with low electromotive force can be appropriately inspected and suppressed. In addition, such an inspection can be performed highly efficiently in a non-contacting state. A cylindrical dry battery can be provided in which the contact failure on the terminal faces is certainly suppressed.

The invention claimed is:

1. A battery terminal inspection apparatus that inspects a contact failure at an outer surface of a positive terminal and a negative terminal of a dry battery, comprising:
    a light-emitting section that makes a light incident on a part to be measured of the outer surface;
    a light-receiving section that detects a reflection state of the light from the part to be measured; and
    a measurement processing section that digitizes the reflection state of the light from the part to be measured based on detection with the light-receiving section,
    wherein evaluation data of the contact failure is obtained with measurement values of the reflection state of the light.

2. A battery terminal inspection apparatus, wherein according to claim 1, gloss level, as the reflection state of the light from the part to be measured, is measured with a received light quantity of a reflected light and the evaluation data of the contact failure is obtained with the measured received light quantity.

3. A battery terminal inspection method, wherein regarding a positive terminal and a negative terminal of a dry battery, an increase of contact resistance due to an oxide film generated on the outer surface thereof or dirt of adherents such as oil is inspected using an apparatus according to claim 1 or 2.

4. A battery terminal inspection method, wherein a received light quantity of the reflected light is measured in the following measurement conditions, by using a digital color differentiation sensor as an apparatus according to claim 1 or 2

[Measurement Conditions]
    Colors of light source: red LED, green LED, blue LED
    Sensor type: red LED, green LED, blue LED light source reflecting type photoelectric sensor attached with amplifier
    Distance from a sensor heard to a sample: 20 mm
    Angle: at right angles to the sensor head
    Measuring spot diameter: 3.5 mm
    Measurement time: 0.5-1 minute
    Standard color face setting: the received light quantity is 300 on a specular surface
    Measurement condition: still.

5. A cylindrical dry battery, wherein an average received light quantity at an outer surface of a positive terminal and a negative terminal is within a range of 20-60 by the received light quantity (300 in a specular surface) that is to be measured with the inspection method according to claim 4.

* * * * *